United States Patent [19]

Hammerling et al.

[11] Patent Number: 4,680,258
[45] Date of Patent: Jul. 14, 1987

[54] PROCESS FOR SEX DETERMINATION IN MAN BY USE OF MONOCLONAL ANTIBODIES TO THE H-Y ANTIGEN

[75] Inventors: Ulrich Hammerling, New York, N.Y.; Gloria C. Koo, Woodbridge, N.J.; Nobuhiko Tada, New York, N.Y.

[73] Assignee: Sloan-Kettering Institute for Cancer Research, New York, N.Y.

[21] Appl. No.: 521,635

[22] Filed: Aug. 9, 1983

Related U.S. Application Data

[63] Continuation of Ser. No. 247,191, Mar. 24, 1981, abandoned.

[51] Int. Cl.$^4$ .................... G01N 33/577; C12N 5/00; C12P 15/00; A61K 39/395
[52] U.S. Cl. .................... 435/7; 435/172.2; 435/240; 435/948; 530/387; 436/548; 436/821; 436/828; 935/103; 935/110
[58] Field of Search ............. 435/7, 172, 64, 4, 172.2, 435/948, 240; 424/85; 436/548, 510, 518, 540, 542, 545, 811, 828, 821; 260/112 R, 112 B; 935/103, 110; 530/387

[56] References Cited

U.S. PATENT DOCUMENTS

| | | | |
|---|---|---|---|
| 4,076,797 | 2/1978 | Davis | 424/1 |
| 4,172,124 | 10/1979 | Koprowski et al. | 424/85 |
| 4,191,749 | 3/1980 | Bryant | 424/85 |
| 4,376,110 | 3/1983 | David et al. | 436/513 |
| 4,511,661 | 4/1985 | Goldberg | 436/548 |

OTHER PUBLICATIONS

Goldberg, et al, "Serological Demonstration of H-Y Antigen on Mouse Sperm", *Nature*, vol. 232, 1971, pp. 478–480.
Ahlstedt et al, "Applications of the ELISA for Determination of Immunoglobulin Class-Specific E. Coli Antibodies", *Scan J. Im,* v. 8, pp. 119–124.
Koo et al, Fetal H-Y Typing Using Human Amniotic Fluid, *Symposium Abst.*, 1982, p. 182.
Koo et al, Hum. Genet., 57: 64–67, (1981).
Krco et al, Science, 193: 1134–1135, (1976).
Kohler et al, Nature, 256: 495–497, (1975).
Galbraith et al, Transplantation, 26(1): 25–27, (1978).
Herzenberg et al, Proc. Nat'l. Acad. Sci., U.S.A., 76(3): 1453–1455, (1979).

*Primary Examiner*—Esther M. Kepplinger
*Attorney, Agent, or Firm*—John P. White

[57] ABSTRACT

Production of anti-H-Y hybridoma cell lines, and the use of the antibodies to determine the presence of H-Y antigen to indicate the sex of the proband inclusive of fetus, newborn and adult humans.

17 Claims, 2 Drawing Figures

PROCESS FOR SEX DETERMINATION IN MAN BY USE OF MONOCLONAL ANTIBODIES TO THE H-Y ANTIGEN

This application is a continuation of application Ser. No. 247,191, filed Mar. 24, 1981, now abandoned.

BACKGROUND

This invention relates to the use of monoclonal antibody to the H-Y antigen for diagnosing the sex of a mammalian and avian cell, i.e. that one can determine whether that cell is derived from an individuum carrying a Y chromosome or not. Therefore, this diagnostic process can determine the gender of individuum of a wide range of species, inclusive, but not limited to, mammals and birds.

In man, in fact all mammals, sex is determined by the inheritance of the Y chromosome. Obviously, this derives from the male, which produces two types of germ cells, Y-bearing and X-bearing spermatozoa. On fertilization with the X-bearing ovum, two types of zygotes (fertilized eggs) result in statistical proportions, usually near 50/50. Zygotes with XX constellation develop to females, whereas those of XY constellation become males. The laws of Genetics therefore generally dictate that all male cells (except haploid germ cells and erythrocytes) carry X and Y chromosomes and those of the female XX chromosomes. Although a reversal of this general rule is noted in some animals e.g. birds, the determination is still applicable although with reversed interpretation.

The secondary (phenotypic) sexual development of the male is under the influence of hormones, however, little is known about the primary (gonadal) sexual development. It is thought that the Y-chromosome directs the production of a product (s) which induces in early embryonal life a cascade of events that lead to the expression of the male phenotype. For instance, there is good evidence that products of the Y chromosome direct undifferentiated gonads to develop towards testis, and this is one of the first crucial events in the aforementioned cascade. It is important to note that in the absence of properly functioning Y products the gonads of mammals follow a preset pathway leading to formation of ovaries. Today the exciting possibility exists that the inducer of testicular differentiation has been identified as the H-Y antigen. This assumption is hypothetical, but it should be mentioned that the following application of this biological principle is not essentially dependent upon the role of H-Y in sex differentiation. It is important to note that most male cells of the mammals, starting with early embryonal age, express the H-Y antigen.

What is the H-Y antigen?

The H-Y antigen was first described by Eichwald and Silmser in 1955 as the antigen responsible for tissue rejection by female mice grafted with tissues of males of the same inbred strains. Hence the only genetic difference was the presence of the Y-chromosome and its products in the transplant donors, and the females reacted against the molecules absent from their own tissues, which were conceived as foreign (consonant with the immunological principle that exposure to products absent from an individuum potentially elicits an immunological reaction). The H-Y molecule is foreign to the female and acts as an antigen to provoke an immune response.

The initial observation of transplant rejection was later corroborated by demonstration of circulating antibody in the females that rejected male tissue grafts (Goldberg et al. 1971).

The availability of conventional antiserum to H-Y antigen has helped to characterize the H-Y antigen.

(1) Serological definition

As already mentioned H-Y antigen is expressed on the majority of tissues of the male. The antigen is widely conserved in ontogeny, meaning that embryonal cells synthesize H-Y, and that cells of the adult continue to synthesize H-Y throughout life. Anti-H-Y antiserum reacts directly with a number of tissues (such as sperm, lymphocytes, fibroblasts, epidermal cells and brain cells) as recognized by assay procedures such as complement-dependant cytotoxicity assay and antibody-binding assays.

(2) Phylogenetic conservation

The startling and unique finding was that anti-H-Y antibody produced in the mouse crossreacts with cells of many vertebrate species inclusive of mammals, birds and amphibia. Thus, H-Y is conserved in an unusually wide phylogenetic range of animals. Such conservation must indicate as essential biological purpose, such as for instance testicular induction. (Wachtel, S. S., *Immunol. Reviews* 33: 33, 1977).

(3) Expression of H-Y in man

Crossreactivity extends to human males, and it is now clear that all males express H-Y. The expression of H-Y is correlated with the genetic sex (i.e. the presence of Y chromosome) and with the presence of testicular tissues and not necessarily with the phenotypic sex. There are ambiguous sex and intersex conditions, which are of concern to society due to the psychological implications. In addition, numerous hereditary diseases are linked with the genetic sex. Thus, evaluation of genetic sex is frequently a necessity for proper diagnosis and this is performed by karyotyping (i.e. microscopic inspection of chromosomes, derived from cells arrested in their division with colcemid) for the presence of the X and presence or absence of Y chromosomes. More recently, this cumbersome karyotyping technique has been supplemented by serological typing for H-Y antigen particularly when there is ambiguity in identifying a minute or ring sex chromosome.

The technical advances, conceptually as well as practically, which make typing feasible for clinical diagnosis are the developments of (a) monoclonal antibodies and (b) novel assay procedures. These are the essence of this invention.

SUMMARY

Murine hybridomas have been developed by fusion of myelomas, such as P3-NS-1-Ag4-1 (Kohler and Milstein, *Nature* 256, 495, 1975) with spleen cells of female mice, such as (but not limited to) C57BL/6 mice, immunized with lymphocytes of males of the same strain. The resulting hybridomas produce anti H-Y monoclonal antibodies which react with male but not the female cells. As H-Y is expressed early on in ontogeny and continues to be expressed throughout life, serological determination of H-Y can serve as a means to identify the gender of an individuum in the sense that a positive reaction signals the presence of Y chromosomes, whereas a negative reaction would be indicative for the absence of H-Y and hence for female genetic sex. Monoclonal anti-H-Y antibodies are superior to conventional sera, and enable the unambiguous assay procedure for presence or absence of H-Y and hence by inference for male versus female sex. The invention of sex determination spans the description of five hybridoma clones, serological assays dependent on these monoclonal antibodies, i.e. processes to detect H-Y antigen on cells of adults and fetuses, and to detect soluble H-Y antigen in amniotic fluid, and, to the extent that H-Y crosses the placenta, in the serum of pregnant women.

DESCRIPTION

Figure 1:
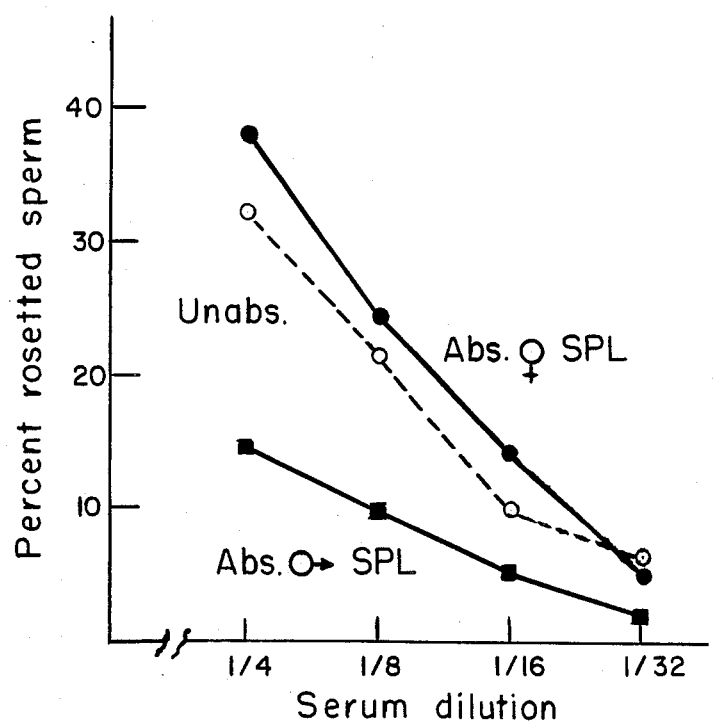
FIG. 1 illustrates a PA-SRBC rosette assay showing the reaction of monoclonal anti-H-Y antibody (12-44) with BALB/c sperm before and after absorption with male and female BALB/c spleen cells (SPL). Each point represents the mean of two experiments.
Figure 2:
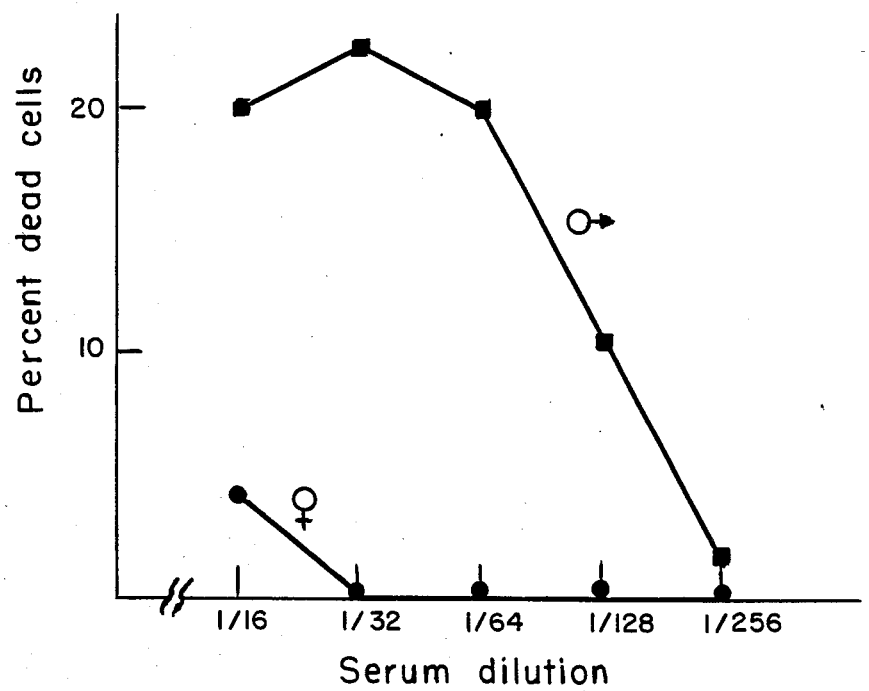
FIG. 2 illustrates the cytotoxicity test showing the reaction of monoclonal anti-H-Y antibody (12-44) with male and female BALB/c lymph node cells. Percent dead cells refers to cytotoxicity index described in material and methods.

Preferred clones 12/44, 12/49, and 6/11, and have been deposited with and are available from the Sloan-Kettering Institute for Cancer Research, 1275 York Avenue, New York, N.Y. 10021, and 145 Boston Post Road, Rye, N.Y. 10580.

Cell lines 12/44, 12/49, and 6/11 have also been deposited with the American Type Culture Collection and bear the following accession numbers:

12/44: HB 9070
12/49: HB 9071
6/11: HB 9072

Production of the murine hybridomas Clones #12/44, 12/49 and 6/11, is described as follows—C57BL/6, or BALB/c mice were hyperimmunized with lymphocytes of C57BL/6, or BALB/c males, respectively. Three days after the last immunization the spleen cells were fused wih murine myeloma cells, (cell line, P3-NS-1-Ag4-1). Out of several hundred hybridoma clones, 5 clones produced antibody which reacted with male cells in the PA-rosette assay of Koo and Goldberg, *J. Immunol. Methods* 23: 197–201 (1978). The cells of these hybridomas were recloned several times. The hybridoma cell lines have been maintained on deposit at Sloan-Kettering Institute for Cancer Research, 1275 York Avenue, New York, NY 10021, under designations corresponding to the monoclonal antibodies produced by each hybridoma as follows: 12/44, 12/49, 6/11, 14/22 and 20/2. Upon granting of the patent, said hybridoma cell lines will be permanently available by deposit with the American Culture Collection, 1230 Parklawn Drive, Rockville, Md. 20852 under ATCC designations corresponding to the above Sloan-Kettering designations. On injection into mice they produced tumors which in turn secreted anti-H-Y antibody. The ascites fluids or sera of tumor bearing mice harbor anti-H-Y antibody. Titers by cytotoxicity on sperm cells range from 1:200 to 1:5000. These anti-H-Y antibodies (#12/44. 12/49 and 6/11) are of IgM class with kappa chains. At least two of these (12/44 and 12/49) differ from one another by idiotype analysis. Serological activity of antibody can be assessed by a number of procedures including but not limited to cytotoxicity, immunofluorescence, PA-rosette assay (despite the fact that anti-H-Y is of IgM class), radioimmunoassay, ELISA assay and radioimmuno- or ELISA inhibition assay. Other inhibition assays involve absorption of cytotoxic antibody by cells, and testing for residual antibody on suitable target cells (i.e. murine sperm) or blockage of anti-H-Y antibody with soluble H-Y, or competition assays using binding site directed, anti-idiotype antibodies (see patent pending #06/195,441).

METHODOLOGY (a) Protein-A-Sheep Red Blood Cell Rosette Assay (PA-SRBC-rosette assay)

Protein A from the cell wall of Staphylococcus Cowan I strain (commercially available from Pharmacia Fine Chemicals, Sweden) binds to the Fc portion of mammalian immunoglobulin. Despite the fact that the available monoclonal H-Y antibodies belong to the IgM class they bind protein A with sufficient avidity. (Rabbit anti-mouse IgM can also be added to improve the assay.) Sheep erythrocytes (SRBC) coupled with PA by chromic chloride are used as indicator cells in the mixed hemadsorption rosette assay of Koo and Goldberg. Test cells (fibroblasts, lymphocytes) to be typed by this method are sensitized with monoclonal anti-H-Y, washed once, and reacted with PA-SRBC. A cell binding three or more PA-SRBC is scored as a rosette.

$$\% \text{ rosettes} = \frac{\Sigma \text{ rosettes}}{\Sigma \text{ (rosettes + non-rosetted cells)}} \times 100$$

Staining with toluidine blue shows that rosettes usually include only a single test cell. This is also a valuable control for distinguishing true rosettes from SRBC aggregates which sometimes occur.

(b) Cytotoxicity assay

Sperm cytotoxicity tests were performed with epididymal sperm according to the method of Goldberg et al, *Nature*, 232 478–480 (1971). Equal volumes of H-Y antiserum, sperm suspension and rabbit serum (complement source) were incubated at 37° C. for 50 minutes in a rocking waterbath. A solution of trypan-blue dye was added during the last 10 minutes of incubation. The tests were placed on ice, and sperm counted in a hamacytometer. Cells that stained with the dye were scored as dead.

In addition to sperm cytotoxicity test, lymphoid cells could also be used as targets in a two step cytotoxicity test. Equal volumes (25 µl) of cells and serum were incubated for 20 minutes at 4° C., before addition of 25 µl of selected rabbit complement (c) (dil. 1:10). The test was further incubated for 40 minutes at 37° C. and assayed for dead cells by staining with trypan blue.

(c) Radiobinding assay

Test cells (lymphoid cells or fibroblasts) are sequentially reacted for 1 hour at 4° C. with monoclonal anti-H-Y antibody and $^{125}$I labelled rabbit anti-mouse IgM. Cells were washed and counted in a gamma scintillation counter. Counts are adjusted to cpm/$10^6$ cells and compared to that obtained with control female and male cells.

(d) ELISA assay (enzyme-linked antibody binding assay)

This is particularly suitable to detect soluble H-Y antigen in a given sample. Reagents required are the monoclonal anti-H-Y antibody, β-galactosidase conjugated rabbit anti-mouse IgM antibody and the substrate NGP (o-nitrophenyl β-D galactopyranoside).

(e) Immunofluorescence

Fluoresceinated rabbit anti-mouse IgM is used to label cells sensitized with anti-H-Y antibody. Evaluation is similar to (c).

(f) Absorption assay

Absorption assay is carried out by mixing 30 μl of diluted antiserum with $10 \times 10^6$ human peripheral white blood cells or $1 \times 10^6$ trypsinized human fibroblasts for 40 mins. on ice. The suspension is centrifuged, the cells discarded and 25 μl of absorbed antiserum is subsequently tested for residual antibody using any of the above assays (a–e) and a known H-Y+ test cell as standard.

(g) Antibody neutralization (inhibition) assay

Antibody neutralization assay to test soluble H-Y antigen or serum in amniotic fluid is performed by using serological assay described above (a–e).

Specificity of murine monoclonal anti-H-Y antibody

The conventional definition of anti-H-Y antibody was used as the criterium for establishment of the specificity of these monoclonal antibodies. Therefore, within the same inbred strain of mice, only male cells reacted with the antiserum. FIG. 1 shows binding a PA-SRBC on BALB/c sperm sensitized with ascites fluid derived from clone 12-44. Absorption with male but not with female BALB/c spleen cells removed the antibody activity from 12-44 ascites fluid. The titer of ascites fluid of clone 12-44 as determined by PA-SRBC test was $\frac{1}{8}$. 12-44 was male-specific, but the titer was unexpectedly low, and the assay was improved by the addition of rabbit-anti-mouse IgM before reacting with PA-SRBC, giving a titer of 1:160. In our experience binding assays using Protein A were not as effective as cytotoxicity assays when IgM antibodies were used. Indeed, using sperm or as target cells in cytotoxicity tests we could demonstrate a titer of 1:5000.

We also attempted cytotoxicity tests with male and female lymphocytes as target cells. Although lymphoid cells express H-Y antigen, as demonstrated by the ability to absorb anti-H-Y reactivity, and by direct reaction with anti-H-Y antibody in staphaureus binding assay (i.e. the PA-SRBC assay) they are not readily lysed by conventional anti-H-Y antiserum and complement. This has been attributed to a low epitope density of H-Y antigen on lymphoid cells. We have, however, used lymph node cells in cytotoxicity assays wih monoclonal 12-44 and have demonstrated a significant difference between male and female cells at a titer of 1:128. This again confirmed that 12-44 was male specific and that it was indeed more powerful than conventional anti-H-Y antibody which could not lyse lymphoid cells.

Reactivity of monoclonal H-Y antibody with human fibroblasts

Using monoclonal anti-H-Y 12-44, H-Y typing of human cells was accomplished using 80 human fibroblasts cultures of males and females. Trypsinized fibroblasts were reacted in suspension with ascites fluid of clone 12-44 at a dilution of 1:4 followed by reaction with PA-SRBC. All 40 male fibroblasts consistently produced a significantly higher percentage of rosettes in PA-SRBC assay when compared to 40 female fibroblasts (Table 1). Therefore, we have established the crossreactivity between murine and human H-Y.

We have extended the investigation to the study of several individuum with abnormal sex chromosomes and have confirmed that monoclonal antibody 12-44 could be used for clinical typing. In direct PA-SRBC assay, fibroblasts gave variable results, but there was a significant difference in the incidence of rosettes ($p \leq 0.01$, n=40) between female and male fibroblasts. The variability was apparently produced by the degree of confluency of cell cultures and the time of trypsinization. We have improved the cells of assay by using cultures at stationary phase which underwent short (less than 5 mins.) trypsinization. Variability was essentially eliminated.

Reactivity of monoclonal H-Y antibody with human peripheral white blood cells (WBC)

Because the presence of Fc receptors on these cells causes high non-specific rosette formation an indirect method has been developed which gives more unambiguous results. Thus, using an absorption assay of anti-H-Y antibody the presence of H-Y on human WBC can be shown with assurance. Citrated whole blood was drawn within 48 hours of testing. 6% dextran in saline (Abbott Laboratory) and 10 units/ml heparin were added to separate the white and red cells (vol. of blood: vol. of dextran=5:1). White blood cells were than washed twice and $10 \times 10^6$ cells were used to absorb 30 μl H-Y antiserum. Residual anti-H-Y activity was then measured by the PA-SRBC assay with BALB/c sperm cells as target cells. (Statistical Analysis Wilconox signed rank test). Table 2 shows the reaction of monoclonal antibody, 12-44, with BALB/c sperm after absorption with WBC from normal male and female individuum and from a patient with Turner's syndrome. Only male cells and not female cells removed anti-H-Y antibody ($p \leq 0.01$, n=5). The patient's cells removed anti-H-Y reactivity, indicating the presence of H-Y antigen.

TABLE 1

PA-SRBC rosette tests showing reactions of monoclonal H—Y antibody (12-44) with fibroblasts cultured from human females and males

| Number of samples | Karyotype | Phenotypic Sex | % Rosettes in PA-SRBC | H—T typing |
|---|---|---|---|---|
| 40 | 46, XY | Male | 22 (10–38)[b] | + |
| 40 | 46, XX | Female | 3 (0–10) | − |
| 2 | 45, X/46, X, −X, +r | Females, Turner's syndrome | 15, 20 | + |
| 1 | 46, XY | Female, gonadal dysgenesis | 30 | + |
| 1 | 45, X/46, X, −X, +min | Female, Turner's syndrome | 14 | + |
| 1 | 46, X, −X, t(X;Y) | Female, Turner's syndrome | 17 | + |

TABLE 1-continued

PA-SRBC rosette tests showing reactions of monoclonal H—Y antibody (12-44) with fibroblasts cultured from human females and males

| Number of samples | Karyotype | Phenotypic Sex | % Rosettes in PA-SRBC | H—T typing |
|---|---|---|---|---|
| 1 | 45, X, +min | Male | 40 | + |

[a] % Rosettes = $\frac{\Sigma \text{ rosetted cells}}{\Sigma \text{ (rosetted + non-rosetted cells)}} \times 100$

[b] Mean values (range)

TABLE 2

PA-SRBC rosette tests showing reactions of monoclonal H-Y antibody 12-44 with sperm of BALB/c mice after absorption with human female or male cells.

| H-Y antiserum absorbed[a] with white blood cells from | % Rosettes[b] | H-Y typing |
|---|---|---|
| 46 XX female | 35 (29-52)[c] | — |
| 46 XY male | 16 (8-22)[c] | + |
| 45, X/46, X, −X, +min, female with Turner's syndrome | 25 | + |

[a] 30 μl of H-Y antiserum diluted 1:4 was absorbed with 10 × 10⁶ white blood cells for 40 min at 4° C.
[b] See footnote in Table 1
[c] Mean values (range) of 5 separate tests Preliminary results obtained with new assays.

(1) Radiobinding assay—using the combination of anti-H-Y antibody and $^{125}$I labelled rabbit anti-mouse IgM, A difference between male and female cells is clearly demonstrated.

TABLE III

Radiobinding assays showing reactions of monoclonal anti-H-Y antibody with human peripheral white blood cells (WBC) and trypsinized fibroblasts

| Karyotype | Sample | cpm/10⁶ cells* |
|---|---|---|
| XY | WBC | 3,441 ± 500 |
| XX | " | 1,341 ± 100 |
| XY | fibroblasts | 3,882 ± 800 |
| XX | " | 578 ± 300 |

*Mean cpm ± S.D. of 3 samples. 1-5 × 10⁶ cells were reacted with 50 μl of anti-H-Y antibody, washed once and reacted with 50 μl of $^{125}$I rabbit anti-IgM. Cells were washed twice, counted, and the bound radioactivity determined by scintillation spectroscopy.

(2) Neutralization assay with amniotic fluids

Amniotic fluids have been tested and clear inhibition of the formation of PA-SRBC rosettes was obtained, when anti-H-Y antibody was first exposed to the amniotic fluid and subsequently used in the PA-SRBC rosette assay with mouse sperm.

TABLE IV

Percent inhibition of PA-SRBC rosettes obtained with amniotic fluids of male and female fetuses*

| Karyotype | % inhibition |
|---|---|
| XY | 40-50 |
| XX | 10-30 |

*25 μl of amniotic fluid incubated with 25 μl of anti-H—Y (diluted at 1:6) at 4° for 30 mins. PA-SRBC rosette assay was subsequently performed on mouse sperm. % inhibition was calculated by the formula $$\left(1 - \frac{\% \text{ PA-SRBC with amniotic fluid}}{\% \text{ PA-SRBC without amniotic fluid}}\right) \times 100.$$

What is claimed is:

1. Hybridoma cell lines selected from the group consisting of ATCC HB 9070, ATCC HB 9071 and ATCC HB 9072 producing monoclonal antibodies 12/44, 12/49, and 11/6 which specifically bind to the H-Y antigen.

2. Process for determining gender of a fetus carried in a female, comprising obtaining a sample of blood or amniotic fluid from the female and measuring the H-Y antigen in said sample by contacting said sample with monoclonal anti-H-Y antibodies selected from the group consisting of 12/44, 12/49, and 6/11 produced by hybridoma cell line ATCC HB 9070, ATCC HB 9071 or ATCC HB 9072 and observing reaction between said sample and said monoclonal antibodies, presence of said reaction indicating that the gender of said fetus is male absence of of said reaction indicating the gender of said fetus is female.

3. Process of claim 2 wherein the step of determining whether or not a reaction occurs comprises a direct radioimmuno assay using radioactive labeled monoclonal anti-H-Y antibodies, or an indirect assay, using unlabeled anti-H-Y antibody and radioactively labeled anti-immunoglobulin.

4. Process of claim 2 wherein the step of determining whether or not a reaction occurs comprises a Protein A rosette binding assay.

5. Process of claim 2 wherein said reaction is detected by enzyme-linked antibody binding assay (ELISA).

6. Process of claim 2 wherein said reaction is detected by an assay selected from the group consisting of direct and indirect immunofluorescence assays.

7. Process of claim 3 wherein the step of determining whether or not a reaction occurs comprises a complement-dependent cytotoxicity reaction.

8. Process of claim 2 wherein the step of determining whether or not a reaction occurs comprises a neutralization assay with cell bound H-Y antigen and further comprises measurement of whether neutralization of anti-H-Y antibody occurs.

9. Process of claim 3 wherein said sample comprises human amniotic cells whereby the presence of H-Y positive cells indicates a male fetus and the absence of H-Y positive cells a female fetus.

10. Process of claim 9 wherein the step of determining whether a reaction occurs comprises an immunofluorescence flow cytometry assay.

11. Process of claim 2 wherein said sample comprises human amniotic fluid whereby the presence of H-Y antigen signals a male fetus and the absence of H-Y a female fetus.

12. Process of claim 2 or 8 wherein said sample comprises serum of a pregnant woman, whereby the presence of H-Y antigen will indicate a male fetus.

13. Process of claim 2 wherein said sample comprises peripheral blood cells of a pregnant woman, whereby the presence of H-Y positive cells with indicate a male fetus.

14. Process of claim 13 wherein the step of determining whether a reaction occurs comprises an immunofluorescence flow cytometry assay.

15. Process of claim 2 wherein the step of determining whether a reaction occurs comprises an immunofluorescence flow cytometry assay.

16. Process of claim 2, wherein the step of determining whether a reaction occurs comprises an assay method selected from the group consisting of radioimmuno assay, enzyme-linked antibody binding assay (ELISA), direct or indirect immunofluorescence assay, and immunofluorescence flow cytometry assay.

17. Monoclonal antibodies which specifically bind to H-Y antigen selected from the group consisting of 12/44, 12/49, and 6/11 produced by hybridoma cell line ATCC HB 9070, ATCC HB 9071 or ATCC HB 9072.

* * * * *